United States Patent [19]

Olivier

[11] Patent Number: 4,917,106
[45] Date of Patent: Apr. 17, 1990

[54] CONDUCTIVE TIPS OF CARDIAC STIMULATION PROBES

[75] Inventor: Stéphane Olivier, Paris, France

[73] Assignee: ELA Medical, Montrouge, France

[21] Appl. No.: 198,987

[22] Filed: May 26, 1988

[30] Foreign Application Priority Data

Jun. 4, 1987 [FR] France ................ 87 07788

[51] Int. Cl.⁴ .............................................. A61N 1/04
[52] U.S. Cl. ................................. 128/785; 128/786
[58] Field of Search ............... 128/642, 784–786, 128/419 P

[56] References Cited

U.S. PATENT DOCUMENTS

| | | | |
|---|---|---|---|
| 4,030,508 | 6/1977 | Thalen | 128/419 P |
| 4,033,357 | 7/1977 | Helland et al. | 128/785 |
| 4,236,529 | 12/1980 | Little | 128/786 |
| 4,566,467 | 1/1986 | Deltaan | 128/784 |
| 4,679,572 | 7/1987 | Baker, Jr. | 128/786 |

FOREIGN PATENT DOCUMENTS 0064289  11/1982  European Pat. Off. ........ 128/419 P Primary Examiner—Lee S. Cohen
Attorney, Agent, or Firm—Darby & Darby

[57] ABSTRACT

Endocardiac probe for a pacemaker, this probe is of the type comprising a helically wound lead (1) enclosed in a flexible sheath (2), with an electrode fitted on the tip of said lead, characterized by said electrode being formed of an annular piece (4) traversed by an attachment member (5–6) comprising a stem (5) engaging inside the windings of the conductor lead (1) and a head (6) securing the electrode (4) in its proper position.

20 Claims, 3 Drawing Sheets

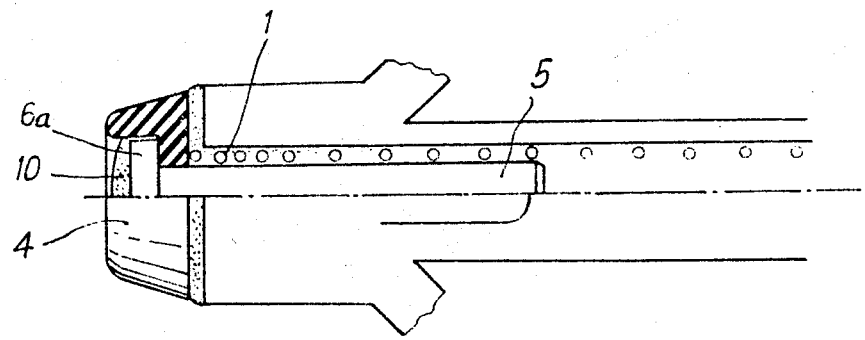
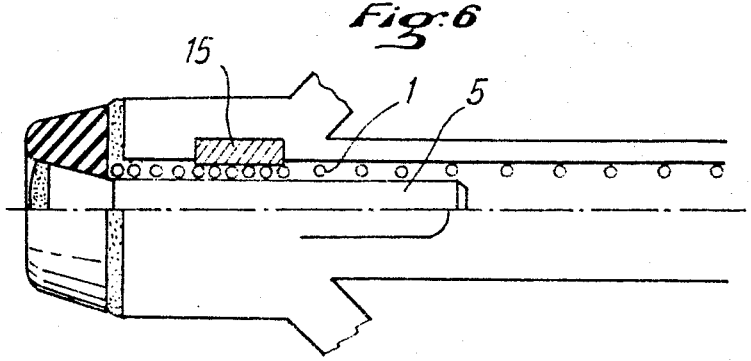
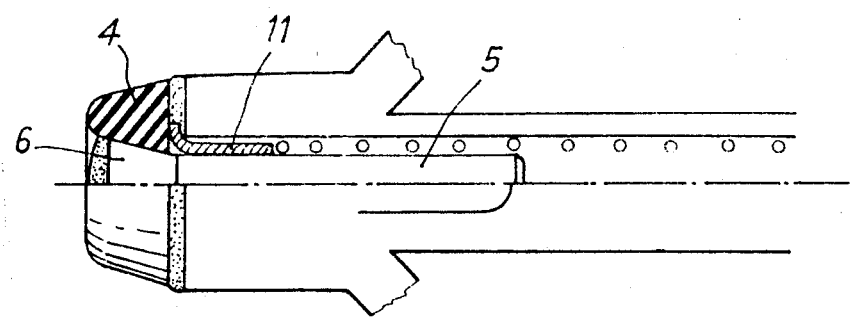

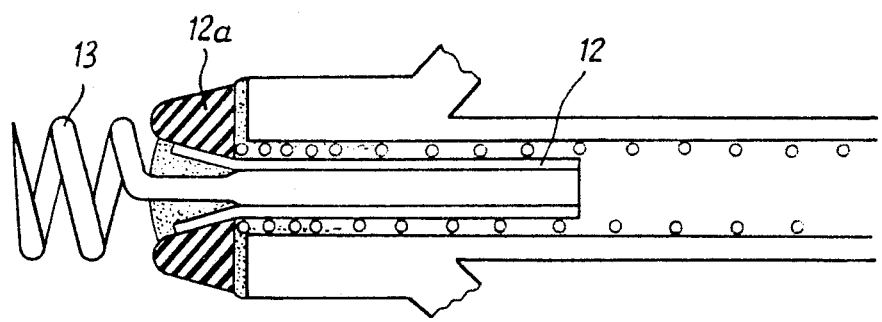
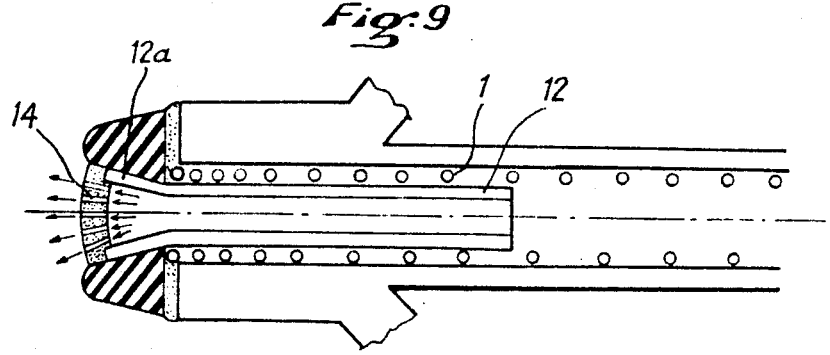
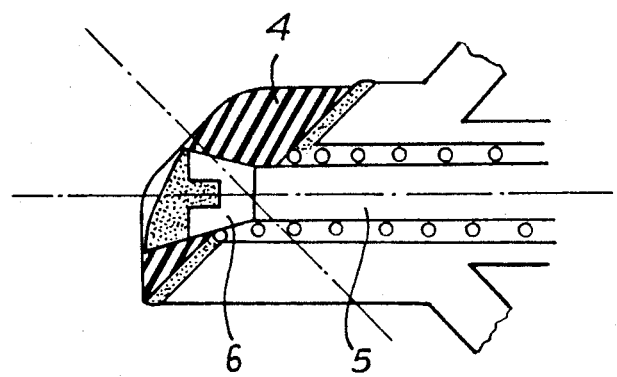

CONDUCTIVE TIPS OF CARDIAC STIMULATION PROBES

This invention relates to improvements to the conductive tips of cardiac stimulation probes.

BACKGROUND OF THE INVENTION

It has been known since many years how to achieve cardiac stimulation by means of an electric signal generator which is usually implanted under the thorax skin and connected to the internal wall of the heart by a lead passing through a vein such as the sub-clavian vein. This lead called either a catheter or an endocardiac probe, is formed of an helically wound metal wire enclosed within a flexible sheath, made for instance of silicone rubber, and ending with a conductive piece intended for being brought into contact with the inner wall of the heart muscle, this piece being the actual electrode.

The utilization of novel types of electrodes made of inorganic materials such as pyrolythic carbon or vitreous carbon, etc., or ceramics having zero plasticity and low tenacity requires a flexible and reliable system for connecting the electrode to the lead. This fixation system will, more often than not, provide for both the mechanical link and the electrical link between the electrode and the conductor. It is moreover desirable that the system being selected should lend itself to an easy mounting, using interchangeable standard elements which will make it possible, more particularly, to place electrodes made of different materials and having different shapes and surfaces. It is worthwhile to be enabled to modulate the electrode surface, for instance to reduce this surface, thereby increasing the local current density and leading to a lowering of the stimulation thresholds and of the energy required for stimulating heartbeats.

SUMMARY OF THE INVENTION

This invention has for its object to provide for these various results. It relates to an endocardiac probe for a heartbeat stimulator or pacemaker, this probe being of the type formed of a spirally wound single-wire or multi-wire lead, arranged inside a flexible sheath, a conductive electrode being placed on the distal end of this lead, said probe being characterized in that the electrode is annular and is traversed by an attachment member comprising a stem engaging the inside of the lead windings and a head effective for holding the electrode in place.

The invention further includes any or all of the following features:

(a) The head of the attachment member forms a stop the shape of which is complementary to the central bore of the annular electrode, this shape being conical, or with a shoulder, or spherical or otherwise.

(b) The fixation of the annular electrode is effected by a resilient wedging between the head of the attachment member and the helically wound conductor.

(c) The fixation of the annular electrode is effected by wedging between the head of the attachment member and a ring.

(d) The attachment member is fixed to the conductor through resilient deformation of the conductor windings by the stem of the said attachment member.

(e) The attachment member is fixed to the conductor by crimping a ring.

(f) The stem of the attachment member is roughened in order to improve its fixation inside the winding.

(g) The attachment member is hollow and is capable of receiving active fixation means for attaching the electrode to the heart muscle wall.

(h) The attachment member is hollow and communicates with the inside of the probe, thereby allowing for liquid products being injected therethrough.

(i) The head of the electrode attachment member is covered with an insulating material.

(j) The head of the electrode attachment member is provided with a slot for allowing this member to be introduced inside the winding by screwing.

(k) The fixation of the annular electrode to the probe tip is supplemented by an adhesive.

(l) The contacting area of the annular electrode may be gradually decreased by successive cutting out.

(m) The attachment member is made wholly or partly of a material being opaque to X-rays.

(n) The annular electrode is made of an inorganic material such as a ceramic or carbon material.

(o) The annular electrode is made of a metallic material such as iridium-alloyed platinum.

As non-limitative examples and for making the invention more easily understood, the appended drawings are illustrating:

FIG. 1 a longitudinal semi-cross sectional view of a first embodiment of the probe according to this invention;

FIG. 2 a view, partly in semi-cross section, of a modified embodiment of the probe of FIG. 1;

FIGS. 3 and 4 two partial views of an electrode;

FIG. 5 illustrates a modified embodiment of the electrode fixation;

FIG. 6 shows a further embodiment of the fixation of the lead to the fixation stem;

FIG. 7 is a view similar to FIG. 1, showing yet another modification of the electrode fixation device;

FIG. 8 is a partial view showing an embodiment of the attachment member allowing an active fixation means to be inserted therein;

FIG. 9 is a partial view showing another embodiment of the attachment member allowing for the injection of liquid products therethrough;

FIG. 10 is a longitudinal semi-cross sectional view illustrating another embodiment of the invention.

DETAILED DESCRIPTION OF THE INVENTION

Figure 1:
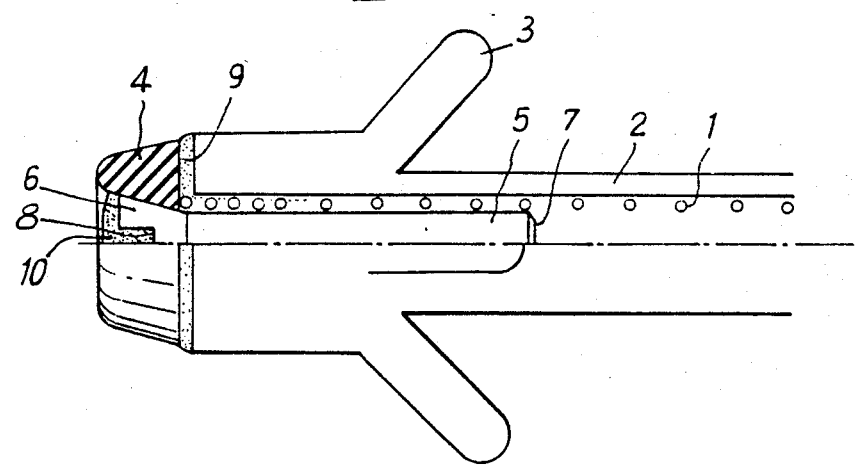

Referring to FIG. 1, it will be seen that the probe is formed, as this is known per se, of a conductive lead 1 which is helically wound and arranged inside a flexible sheath 2 made for instance of silicone rubber and which may advantageously be provided with small barbs 3, also made of silicone rubber.

According to this invention, the actual probe, that is the piece made of a conductive material which is intended to contact the inner wall of the heart muscle in order to transmit to this muscle the stimulating electrical signal, is formed of an annular piece 4 having a substantially trapeze-shaped cross-section.

There is an attachment member comprising a stem 5 which engages inside the lead winding 1 and a head 6 which locks said annular piece 4 in place.

In the example shown in FIG. 1, this head 6 is formed of a frustum, the slope of which is equal to the slope of the inner wall of the annular piece 4 so as to lock said piece firmly in place by wedging. This locking effect implies that the stem 5 will in turn be firmly locked inside the winding 1. For this purpose, the diameter of stem 5 should preferably be slightly larger than the internal diameter of said winding 1. The locking effect may be further enhanced by roughening the surface of stem 5 by any suitable method, such as by sandblasting.

The tip 7 of stem 5 forms a stop so that when a spindle is used for the insertion of the probe, this stop will prevent this spindle from passing through the distal end of the probe.

The stem 5 may be pushed forcibly inside the winding 1 or else be inserted therein by screwing, in which case the head 6 will advantageously be provided with a slot 8 for receiving a screwdriver blade.

Preferably, the fixation of the electrode 4 will be supplemented by using an adhesive 9 which will be interposed between the base of the annular piece and the end of the probe.

The head 6 of the attachment member is moreover covered with a layer of insulating material 10, which may be the same material as the one used for the adhesive 9.

The effect of this insulating layer 10 is to make the central portion of electrode 4 non-conductive, thus increasing the electric current density through the surface thereof.

Figure 2:
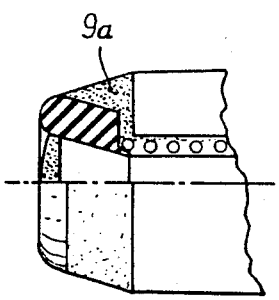
Figure 3:
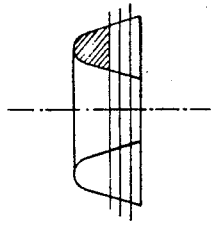
Figure 4:
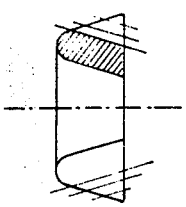

The conductive area of electrode 4 may also be reduced in the manner shown in FIG. 2-4 by making cut-outs either horizontally (FIG. 3) or obliquely (FIG. 4). In the case of a lateral oblique cut-out of the type shown in FIG. 4, the conductive material being thus removed may advantageously be replaced by adhesive material 9a, as shown in FIG. 2.

FIGS. 5, 6 and 7 show three different embodiments of the fixation of the annular electrode 4 by means of the attachment member 5-6.

From FIG. 5 it will be seen that the stem 5 carries a flat head 6a while the electrode 4 is formed with an internal shoulder inside which said flat head 6a will engage: electrode 4 will then be locked between the flat head 6a and the tip of winding 1.

From FIG. 6 it will be seen that the conductor 1 is firmly maintained on the stem 5 of the attachment member by crimping the additional ring 15.

In FIG. 7 the electrode 4 is clamped between the head 6 and an additional clip 11 which is crimped around stem 5.

FIGS. 8 and 9 represent two modified embodiments in which the attachment member of FIG. 1 is a hollow tube 12, the outer end 12a of which is flared. This terminal portion 12a fulfills the same function as the frusto-conical head 6 of FIG. 1 while the cylindrical portion 12 fulfills the same function as the stem 5. This arrangement will make it possible, as shown in FIG. 8, to attach inside the attachment member 12 an active fixation means 13 which may be a helix-shaped piece similar to a cork-screw or a hook. These active fixation means are known per se. This arrangement also makes it possible, according to the embodiment shown in FIG. 9, to close the opening of the outer end 12a of the attachment member with a permeable membrane 14, through which a liquid or a gel may be caused to diffuse.

FIG. 10 represents a modified embodiment of the electrode 4 in which the axis of the attachment member 5-6 does not coincide with the axis of electrode 4. In fact, this former axis may be non-concentric to the electrode and may also be inclined. An arrangement of this kind may prove advantageous, for instance when the probe comprises a tip which is folded back in a J-shaped configuration so as to fit against the apex of an auricle.

I claim:

1. An endocardiac probe for a heart stimulator comprising a helically wound conductive lead arranged inside a flexible sheath, an annular electrode having a central orifice and being electrically connected at a distal end of said lead, an attachment member comprising a stem engaging with and inside of the conductive lead and a head securing the electrode in place, the head forming a stop having a shape complementary to the central orifice of the annular electrode.

2. A probe according to claim 1, wherein the head is coated with a layer of insulating material.

3. A probe according to claim 1, in which the head of the attachment member is frusto-conical and fits with a corresponding frusto-conical shape of the central orifice of the annular electrode.

4. A probe according to claim 1, in which the head of the attachment member is flat and rests against a circular shoulder of a corresponding shape formed in the central orifice of the annular electrode.

5. A probe according to claim 1, in which a clip is crimped around the stem of the attachment member so that that annular electrode will be locked between the head of said attachment member and said clip.

6. A probe according to claim 1, wherein the lead has lead windings, the attachment member being fixed to the lead by an elastic tightening of the lead windings on the stem of said attachment member.

7. A probe according to claim 1, wherein the head of the attachment member is provided with a slot for allowing said member to be screwed inside the windings of the lead.

8. A probe according claim 1, wherein the lead has lead winding, said windings of the lead are tightened over the stem of the attachment member by means of a crimped ring.

9. A probe according to claim 8, wherein the head of the attachment member is provided with a slot for allowing said member to be screwed inside the windings of the lead.

10. A probe according to claim 1, wherein the attachment member is formed of a hollow tube with a flared end.

11. A probe according to claim 10, wherein the hollow tube includes an active fixation element.

12. A probe according to claim 10, wherein the flared end of the hollow tube is occluded by a porous membrane through which a liquid may be injected or diffused.

13. A probe according to claim 1, wherein the outer surface of the stem is roughened, for instance by sandblasting.

14. A probe according to claim 1 further comprising a layer of adhesive is interposed between a base of the electrode and a tip of the probe.

15. A probe according to claim 1, wherein the annular electrode includes successive cut-outs.

16. A probe according to claim 1, wherein an axis of the annular electrode is oblique relatively to an axis of the attachment member.

17. A probe according to claim 1, wherein the attachment member is opaque to X-rays.

18. A probe according to claim 1, wherein the annular electrode is made of an inorganic material.

19. A probe according to claim 1, wherein the annular electrode is made of a metallic material.

20. An endocardiac probe for a heart stimulator comprising:
 a helically wound conductor lead arranged inside a flexible sheath;
 an annular electrode electrically connected at a distal end of said lead;
 a stem engaging with and inside of said conductive lead; and
 a head extending from an end of said stem and pressing against said electrode so that said electrode is wedged between said head and said distal end of said conductive lead.

* * * * *